US012637700B2

(12) United States Patent
Jung et al.

(10) Patent No.: US 12,637,700 B2
(45) Date of Patent: May 26, 2026

(54) METABOLIC PATHWAY FOR PRODUCING ITACONIC ACID AND METHOD FOR PRODUCING ITACONIC ACID USING SAME

(71) Applicant: POSTECH RESEARCH AND BUSINESS DEVELOPMENT FOUNDATION, Pohang-Si (KR)

(72) Inventors: Gyoo Yeol Jung, Pohang-si (KR); Dae Yeol Ye, Miryang-si (KR); Myung Hyun Noh, Seoul (KR); Myeong Won Min, Incheon (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 352 days.

(21) Appl. No.: 18/572,361

(22) PCT Filed: Feb. 28, 2022

(86) PCT No.: PCT/KR2022/002865
§ 371 (c)(1),
(2) Date: Dec. 20, 2023

(87) PCT Pub. No.: WO2023/003118
PCT Pub. Date: Jan. 26, 2023

(65) Prior Publication Data
US 2024/0287551 A1 Aug. 29, 2024

(30) Foreign Application Priority Data
Jul. 19, 2021 (KR) ........................ 10-2021-0094298

(51) Int. Cl.
*C12P 7/44* (2006.01)
*C12N 9/10* (2006.01)
(Continued)

(52) U.S. Cl.
CPC .............. *C12P 7/44* (2013.01); *C12N 9/1029* (2013.01); *C12N 9/90* (2013.01); *C12N 15/70* (2013.01);
(Continued)

(58) Field of Classification Search
None
See application file for complete search history.

(56) References Cited

U.S. PATENT DOCUMENTS

2017/0096690 A1 4/2017 Boelker et al.

FOREIGN PATENT DOCUMENTS

KR 10-1973001 4/2019
WO 2009014437 1/2009

OTHER PUBLICATIONS

Atsumi S, Liao JC. Directed evolution of Methanococcus jannaschii citramalate synthase for biosynthesis of 1-propanol and 1-butanol by *Escherichia coli*. Appl Environ Microbiol. Dec. 2008;74(24):7802-8. doi: 10.1128/AEM.02046-08. Epub Oct. 24, 2008. PMID: 18952866; PMCID: PMC2607174. (Year: 2008).*
(Continued)

*Primary Examiner* — Evelyn Y Pyla
*Assistant Examiner* — Jagamya Vijayaraghavan
(74) *Attorney, Agent, or Firm* — LEX IP MEISTER, PLLC

(57) ABSTRACT

The present invention relates to a novel metabolic pathway for producing itaconic acid and a recombinant microorganism, for producing itaconic acid, into which the metabolic pathway is introduced. It has been confirmed that the recombinant microorganism, for producing itaconic acid, into which the novel itaconic acid metabolic pathway is introduced, according to the present invention, significantly increases the production and yield of itaconic acid. In addition, as the recombinant microorganism for producing
(Continued)

itaconic acid of the present invention uses an intermediate material of glycolysis rather than an intermediate material of the TCA cycle, the recombinant microorganism can further increase the production yield of itaconic acid through further improvement. Accordingly, the novel metabolic pathway for producing itaconic acid and the recombinant microorganism into which the metabolic pathway is introduced can increase the economic feasibility of itaconic acid, and thus can be variously used in industrial fields for synthetic resins, latexes, food additives, and the like in which itaconic acid is utilized.

13 Claims, 4 Drawing Sheets

Specification includes a Sequence Listing.

(51) Int. Cl.
  *C12N 9/90*    (2006.01)
  *C12N 15/70*   (2006.01)
(52) U.S. Cl.
  CPC ................. *C12Y 203/01182* (2013.01); *C12Y 503/03006* (2013.01)

(56)        References Cited

OTHER PUBLICATIONS

Joseph P. Webb et al., "Efficient bio-production of citramalate using an engineered *Escherichia coli* strain", Microbiology 2018;164:133-141, DOI 10.1099/mic.0.000581.

Björn-Johannes Harder et al., "Model-based metabolic engineering enables high yield itaconic acid production by *Escherichia coli*", Metabolic Engineering 38 (2016) 29-37, Jun. 4, 2016.

Panakova M., "Itaconate production by Ustilago maydis; the influence of genes and cultivation conditions", Oct. 10, 2013 XP055202557, total 112 pages.

Xianghao Wu et al, "Production of citramalate by metabolically engineered *Escherichia coli*", Biotechnology and Bioengineering, vol. 113, No. 12, Dec. 1, 2016 (Dec. 1, 2016), pp. 2670-2675.

Velarde M. et al, "Crystal structure and putative mechanism of 3-methylitaconate-Δ-isomerase from Eubacterium barkeri", Journal of molecular biology , vol. 391, No. 3, Aug. 21, 2009 (Aug. 21, 2009), pp. 609-620.

Vuoristo K.S., "Metabolic engineering of *Escherichia coli* for itaconate production", PhD thesis, Wageningen University, Feb. 12, 2016 (Feb. 12, 2016), total 163 pages.

EPO, European search report of the corresponding EP patent application. No. EP 22 84 5990, dated Apr. 3, 2025, total 9 pages.

* cited by examiner

METABOLIC PATHWAY FOR PRODUCING ITACONIC ACID AND METHOD FOR PRODUCING ITACONIC ACID USING SAME

TECHNICAL FIELD

The present invention relates to a novel metabolic pathway for producing itaconic acid and a recombinant microorganism, for producing itaconic acid, into which the metabolic pathway is introduced.

BACKGROUND ART

Itaconic acid is dicarboxylic acid consisting of five carbons, and may be used as a precursor for the synthesis of various polymer materials such as plastics and latex due to its structural characteristics to have great industrial value. Accordingly, in 2004, itaconic acid was selected as Top 12 bio-based platform chemicals by the United States Department of Energy.

Biological production of itaconic acid may be achieved through *Aspergillus terreus*, which produces itaconic acid by itself in nature, but due to the unknown characteristics of the strain, a fermentation process is difficult to be handled and a lot of costs is also consumed. In addition, the *Aspergillus terreus* is difficult to genetically manipulate for improvement, and difficult to control the production of various by-products rather than itaconic acid, so that there is a limitation that a lot of costs is consumed during the purification process.

Accordingly, in order to produce itaconic acid more efficiently, research has been actively conducted to construct recombinant microorganisms for producing itaconic acid. The most conducting research is to produce itaconic acid more efficiently through *Escherichia coli*, a microorganism that is easy to genetically manipulate due to strain characteristics. It has been confirmed that itaconic acid may be produced through heterologous expression of cis-aconitate decarboxylase (CAD) from *Aspergillus terreus* in *E. coli*, but since the enzyme expression and activity during heterologous expression were very low compared to homologous expression, it was difficult to produce itaconic acid in high yield. In addition, in the case of existing production circuits, TCA cycle intermediates are used as precursors, but the accumulation of TCA intermediates in *E. coli* is difficult, so that there is a limit to production.

DISCLOSURE

Technical Problem

Therefore, in order to solve the problems of the related art as described above, the present inventors have constructed a novel itaconic acid metabolic pathway of using intermediate materials of glycolysis rather than an itaconic acid production method of using intermediate materials of the TCA cycle. In addition, the present inventors confirmed that a recombinant microorganism into which the metabolic pathway is introduced had excellent itaconic acid productivity and then completed the present invention.

Therefore, an object of the present invention is to provide an expression cassette for introducing an itaconic acid production pathway including a CimA3.7 gene consisting of the nucleotide sequence of SEQ ID NO: 1 and an Mii gene consisting of the nucleotide sequence of SEQ ID NO: 2.

Another object of the present invention is to provide a recombinant vector for producing itaconic acid including the expression cassette for introducing the itaconic acid production pathway.

Yet another object of the present invention is to provide a recombinant microorganism for producing itaconic acid into which the recombinant vector for producing itaconic acid is introduced and a method for producing itaconic acid using the recombinant microorganism.

Technical Solution

In order to achieve the object, an aspect of the present invention provides an expression cassette for introducing an itaconic acid production pathway including a CimA3.7 gene consisting of the nucleotide sequence of SEQ ID NO: 1 and an Mii gene consisting of the nucleotide sequence of SEQ ID NO: 2.

Another aspect of the present invention provides a recombinant vector for producing itaconic acid including the expression cassette for introducing the itaconic acid production pathway.

Yet another aspect of the present invention provides a recombinant microorganism into which the recombinant vector for producing itaconic acid is introduced.

Yet another aspect of the present invention provides a method for producing itaconic acid including culturing the recombinant microorganism for producing itaconic acid.

Advantageous Effects

According to the present invention, it has been confirmed that the recombinant microorganism, for producing itaconic acid, into which the novel itaconic acid metabolic pathway is introduced, significantly increases the production and yield of itaconic acid. In addition, as the recombinant microorganism for producing itaconic acid of the present invention uses an intermediate material of glycolysis rather than an intermediate material of the TCA cycle, the recombinant microorganism can further increase the production yield of itaconic acid through further improvement. Accordingly, the novel metabolic pathway for producing itaconic acid and the recombinant microorganism into which the metabolic pathway is introduced can increase the economic feasibility of itaconic acid, and thus can be variously used in industrial fields for synthetic resins, latexes, food additives, and the like in which itaconic acid is utilized.

BEST MODE OF THE INVENTION

Figure 1:
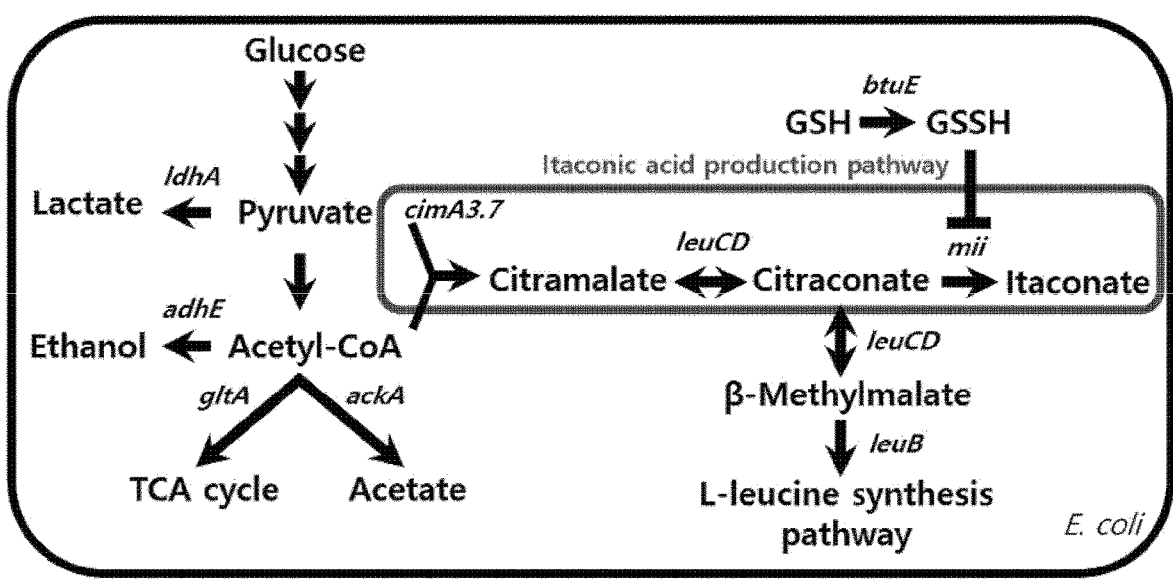
FIG. 1 is a diagram illustrating a novel itaconic acid production pathway in *E. coli* according to the present invention.

Hereinafter, the present invention will be described in detail.

According to an aspect of the present invention, the present invention provides an expression cassette for introducing an itaconic acid production pathway including a CimA3.7 gene consisting of the nucleotide sequence of SEQ ID NO: 1 and an Mii gene consisting of the nucleotide sequence of SEQ ID NO: 2 and a recombinant vector for producing itaconic acid including the expression cassette.

In the present invention, the itaconic acid is dicarboxylic acid consisting of 5 carbons, and is used as a precursor for polymer synthesis, such as plastic and latex due to structural characteristics thereof.

In the present invention, a (R)-citramalate synthase (CimA) gene is a (R)-citramalate synthase (CimA) derived from *Methanococcus jannaschii*, which is known to synthesize citramalic acid from pyruvic acid and acetyl coenzyme A. In addition, it is known that CimA3.7, improved based on the enzyme, has improved enzyme activity and is not subject to feedback inhibition. The CimA3.7 gene of the present invention is consisting of the nucleotide sequence of SEQ ID NO: 1.

In the present invention, it is reported that the 3-methylitaconate isomerase (Mii) gene has the activity of converting methylitaconate derived from *Eubacterium barkeri* to dimethylmaleate. The Mii gene of the present invention is consisting of the nucleotide sequence of SEQ ID NO: 2.

In the present invention, a 3-isopropylmalate dehydratase (LeuCD) gene is a 3-isopropylmalate dehydratase present in *E. coli* and also has a characteristic of converting citramalic acid to citraconic acid. The LeuC and LeuD genes of the present invention are consisting of the nucleotide sequences of SEQ ID NOs: 3 and 4, respectively.

In an embodiment of the present invention, the expression cassette may preferably further include a 5' UTR consisting of the nucleotide sequence of SEQ ID NO: 12 or 13.

In the present invention, the 5' untranslated region (UTR) is an untranslated region at 5' end and 3' end of mRNA, and in general, the 5' untranslated region (5' UTR) of mRNA performs various functions in the gene expression process, but among the functions, the largest feature is involved in regulating mRNA translation efficiency. It has been reported that a nucleotide sequence of the 5' UTR present in an adjacent upper portion of a translation initiation codon affects the efficiency of a translation step, and the length of the 5' UTR consists of 100 bases or more of nucleotide, and the length of the 3' UTR consist of several kilobases longer therethan. In addition, it have been reported results of studies on sequences belonging to the 5' UTR, which may be referred to as ribosome binding site sequences even in eukaryotes, not at a fixed position, such as a Shine-Dalgarno sequence, which was known as a ribosome binding site sequence located in the 5' UTR in prokaryotes.

In an embodiment of the present invention, the expression cassette may preferably further include a Tac promoter consisting of the nucleotide sequence of SEQ ID NO: 11.

In the present invention, the expression cassette refers to a unit cassette that includes a promoter and a gene encoding a target protein and may be expressed to produce the target protein operably linked to the downstream of the promoter. Various factors capable of helping the efficient production of the target protein may be included inside or outside such an expression cassette. Specifically, in the target protein expression cassette, the gene encoding the target protein may be operably linked to the downstream of a promoter sequence.

In addition, variants of the gene are also included within the scope of the present invention. Specifically, the gene has a sequence homology of 70% or more, more preferably 80% or more, even more preferably 90% or more, and most preferably 95% or more with a nucleotide sequence represented by SEQ ID NO. corresponding to each gene, and means a sequence that exhibits substantially the same physiological activity. The "% of sequence homology" with a polynucleotide is determined by comparing two optimally arranged sequences with a comparison region, and a part of a polynucleotide sequence in the comparison region may include addition or deletion (i.e., gap) compared to a reference sequence (not including addition or deletion) for an optimal alignment of the two sequences.

The 'operably linked' means that the gene sequence and the promoter sequence are functionally linked to each other so that a nucleic acid sequence having the promoter activity of the present invention initiates and mediates the transcription of the gene encoding the target protein. The operable linkage may be prepared using genetic recombination techniques known in the art, and site-specific DNA cleavage and linkage may be prepared using cleavage and linkage enzymes in the art, but are not limited thereto. That is, the 'recombinant gene expression cassette' may be inserted into a chromosome of a host cell and used to prepare a recombinant microorganism, and it is obvious for those skilled in the art to which the present invention pertains to have the same effect as the case of introducing the recombinant vector into the host cell as described above even though the recombinant gene expression cassette is inserted into the genomic chromosome of a host cell. As a method of inserting the recombinant gene expression cassette into the chromosome of the host cell, conventionally known genetic manipulation methods may be used. As an example, there is a method using a retrovirus vector, an adenovirus vector, an adeno-associated virus vector, a herpes simplex virus vector, a poxvirus vector, a lentiviral vector, or a non-viral vector.

In the present invention, the vector refers to a genetic construct including a nucleotide sequence of a gene operably linked to a suitable regulatory sequence so as to express a target gene in a suitable host. The regulatory sequence may include a promoter capable of initiating transcription, any operator sequence for regulating such transcription, and sequences for regulating termination of transcription and translation. The vector of the present invention is not particularly limited as long as the vector is replicable in cells, and may use any vector known in the art, for example, a plasmid, a cosmid, a phage particle, or a viral vector.

In the present invention, when a coding gene of a target polypeptide to be expressed is operably linked, the recombinant vector may be used as an expression vector of a target polypeptide capable of expressing the target polypeptide with high efficiency in a suitable host cell, and the recombinant vector can be expressed in a host cell. The host cell may preferably be a eukaryotic cell, and expression regulatory sequences such as a promoter, a terminator, and an enhancer, sequences for membrane targeting or secretion, etc. are appropriately selected according to a type of host cell and may be variously combined depending on a purpose.

According to another aspect of the present invention, the present invention provides a recombinant microorganism into which the recombinant vector for producing itaconic acid is introduced.

In the present invention, the recombinant microorganism refers to a microorganism transformed with the recombinant vector of the present invention. In the present invention, the 'transformation' means introducing a vector including the promoter according to the present invention or further including the gene encoding the target protein into a host cell. In addition, a gene encoding the transformed target protein may be inserted and located into the chromosome of the host cell or located outside the chromosome, as long as the gene may be expressed in the host cell.

In the present invention, one or a plurality of recombinant vectors may be introduced into the recombinant microorganism for producing itaconic acid, and each of the one or the plurality of recombinant vectors may be introduced into the microorganism. In addition, the recombinant vectors may be sequentially introduced into the microorganism, or may also be introduced in a mutually reversed order.

In an embodiment of the present invention, the recombinant microorganism for producing itaconic acid may be characterized to be selected from the group consisting of bacteria, yeast, and fungi, and may preferably be microorganisms of the genus *Escherichia*, and more preferably *Escherichia coli*.

In an embodiment of the present invention, a wild-type *E. coli* W strain having resistance to acetate in *E. coli* was used.

In an embodiment of the present invention, the recombinant microorganism preferably has a LeuC gene and a LeuD gene to be overexpressed, which was referred to as a recombinant strain WT. In the recombinant strain WT, CimA3.7 and Mii genes are introduced and the LeuCD gene is overexpressed.

In a preferred embodiment of the present invention, the recombinant microorganism is preferably introduced with a recombinant vector including an expression cassette for overexpressing LeuCD containing a Tac promoter and a 5' UTR.

In an embodiment of the present invention, the expression cassette for overexpressing LeuCD preferably includes a Tac promoter consisting of the nucleotide sequence of SEQ ID NO: 11 and a 5' UTR consisting of the nucleotide sequence of SEQ ID NO: 14, but is not limited thereto.

In an embodiment of the present invention, the recombinant microorganism is preferably a recombinant microorganism in which a btuE gene consisting of the nucleotide sequence of SEQ ID NO: 5 is further deleted from the WT strain, and more preferably, the btuE gene consisting of the nucleotide sequence of SEQ ID NO: 5 is deleted. The strain was referred to as a recombinant strain B. In the recombinant strain B, the CimA3.7 and Mii genes are introduced, the LeuCD gene is overexpressed, and the btuE gene is deleted.

In an embodiment of the present invention, the recombinant microorganism is preferably a recombinant microorganism in which a LeuB gene consisting of the nucleotide sequence of SEQ ID NO: 6 is deleted from the recombinant strain B, which was referred to as a recombinant strain BL. In the recombinant strain BL, the CimA3.7 and Mii genes are introduced, the LeuCD gene is overexpressed, and the btuE and LeuB genes are deleted.

In an embodiment of the present invention, in the recombinant microorganism, at least one gene selected from the group consisting of an ldhA gene consisting of the nucleotide sequence of SEQ ID NO: 7; and an adhE gene consisting of the nucleotide sequence of SEQ ID NO: 8 is preferably deleted from the recombinant strain BL. More specifically, in the recombinant strain B, (i) the strain from which the ldhA gene was deleted was referred to as a recombinant strain BLL, (ii) the strain from which the adhE gene was deleted was referred to as a recombinant strain BLA, and (iii) the strain from which the ldhA and adhE genes were deleted was referred to as a recombinant strain BLLA.

In an embodiment of the present invention, in the recombinant microorganism, preferably, both the ldhA gene consisting of the nucleotide sequence of SEQ ID NO: 7; and the adhE gene consisting of the nucleotide sequence of SEQ ID NO: 8 are deleted, and an ackA gene consisting of the nucleotide sequence of SEQ ID NO: 9 is further deleted. In other words, the recombinant microorganism is a recombinant microorganism in which the ackA gene was deleted from the recombinant strain BLLA, which was referred to as a recombinant strain BLLAA.

In an embodiment of the present invention, the recombinant microorganism is preferably a recombinant microorganism in which a gltA gene consisting of the nucleotide sequence of SEQ ID NO: 10 is deleted from the recombinant strain BLLAA, which was referred to as a recombinant strain BLLAAG.

According to yet another aspect of the present invention, the present invention provides a method for producing itaconic acid including culturing the recombinant microorganism for producing itaconic acid.

The medium and other culture conditions used for culturing the microorganism of the present invention may be used with any medium to be used for culturing conventional microorganisms of the genus *Escherichia*, but need to suitably satisfy the requirements of the microorganism of the present invention. Preferably, the microorganism of the present invention is cultured in a conventional medium containing suitable carbon sources, nitrogen sources, amino acids, vitamins, etc. under aerobic conditions while controlling temperature, pH, and the like.

In a preferred embodiment of the present invention, the medium may include glucose, pyruvate, etc. as the carbon sources. As the inorganic compound, sodium chloride, calcium chloride, iron chloride, magnesium sulfate, iron sulfate, manganese sulfate, calcium carbonate, and the like may be used, and in addition, amino acids, vitamins, suitable precursors, and the like may be included. These media or precursors may be added to a culture medium in a batch or continuous culture.

During the culture, a compound such as ammonium hydroxide, potassium hydroxide, ammonia, phosphoric acid, and sulfuric acid is added to the culture medium by a proper method to adjust the pH of the culture medium. In addition, during the culture, the generation of bubbles may be suppressed by using an anti-foaming agent such as fatty acid polyclinic ester. Further, in order to maintain an aerobic condition of the culture medium, oxygen or oxygen-containing gases may be injected into the culture medium, and in order to maintain anaerobic and aerobic conditions, gases are not injected or nitrogen, hydrogen, or carbon dioxide gas may be injected.

The temperature of the culture medium may be set usually 27° C. to 37° C., preferably 30° C. to 35° C. The culture period may be continued until a desired production of a useful material is obtained, preferably for 10 to 100 hours.

The method may further include purifying or recovering the produced itaconic acid in the culturing step of the present invention, and a method for recovering the itaconic acid from the microorganism or culture medium may be used with methods known in the art, such as centrifugation, filtration, anion exchange chromatography, crystallization, and HPLC, but is not limited to these examples.

The recovering step may include a purification process, and those skilled in the art may select and utilize various known purification processes as needed.

Duplicated contents are omitted in consideration of the complexity of the present specification, and terms not defined otherwise in the present specification have the meanings commonly used in the art to which the present invention pertains.

MODES FOR THE INVENTION

Hereinafter, the present invention will be described in more detail through Examples. These Examples are just illustrative of the present invention, and it will be apparent to those skilled in the art that it is not interpreted that the scope of the present invention is limited to these Examples.

Example 1. Construction of Novel Itaconic Acid Production Pathway and Construction of Recombinant Microorganism into which Itaconic Acid Production Pathway was Introduced By using the substrate nonspecificity of a 3-methylitaconate isomerase (Mii) gene, a novel biosynthetic pathway of converting citraconate to itaconate was constructed by expressing CimA3.7 (SEQ ID NO: 1) and Mii (SEQ ID NO: 2) genes. The novel biosynthetic pathway was illustrated in FIG. 1.

Specifically, the CimA3.7 and Mii genes were expressed in *E. coli* W by using a recombinant expression cassette including a Tac promoter and a synthetic 5' UTR. A control group and constructed strains WC and WCM were as follows.

Control group: Wild-type *E. coli* W
WC: *E. coli* W introduced with CimA3.7 gene (SEQ ID NO: 1)
WCM: *E. coli* W introduced with CimA3.7 (SEQ ID NO: 1) and Mii (SEQ ID NO: 2) genes

Example 2. Identification of Production of Citramalate and Itaconate by Recombinant Microorganism into which Novel Itaconic Acid Production Pathway was Introduced In order to confirm the production of itaconate through a recombinant microorganism into which the novel itaconic acid production pathway was introduced, the constructed strains WC and WCM were cultured. Specifically, each of the three strains was cultured on a solid LB agar plate to obtain individual colonies. The obtained individual colonies were cultured for about 12 hours in a test tube under conditions of 37° C. and 200 rpm. The cultured strains were inoculated at a 1/100 dilution into 20 mL of a M9 medium contained in a 300 mL round flask, added with IPTG at a concentration of 1 M, and then cultured under conditions of 30° C. and 200 rpm. Then, when an $OD_{600}$ value reached 1 to 2, the strains were inoculated into 20 mL of the M9 medium contained in the 300 mL round flask to become the $OD_{600}$ value of 0.05, and added with IPTG at a concentration of 1 M. Thereafter, the strains were cultured under conditions of 30° C. and 200 rpm. The M9 medium used in Example 2 was added with 20 g/L of glucose and 5 g/L of a yeast extract. During culture, the pH was maintained at 7.0 using 10 M NaOH every 6 hours. After 24 hours of the culture, 1 mL of the culture medium was centrifuged to separate the cultured cells from the culture medium, and then the supernatant culture medium was taken and quantitatively analyzed using HPLC. The HPLC analysis was performed using an Aminex HPX-87H column as a stationary phase and 5 mM of a sulfuric acid aqueous solution as a mobile phase under a condition of a mobile phase rate of 0.6 mL per minute, and a Shodex RI-101 instrument was used for detection. The results of producing the citramalate and itaconate were illustrated in FIG. 2.

Figure 2:
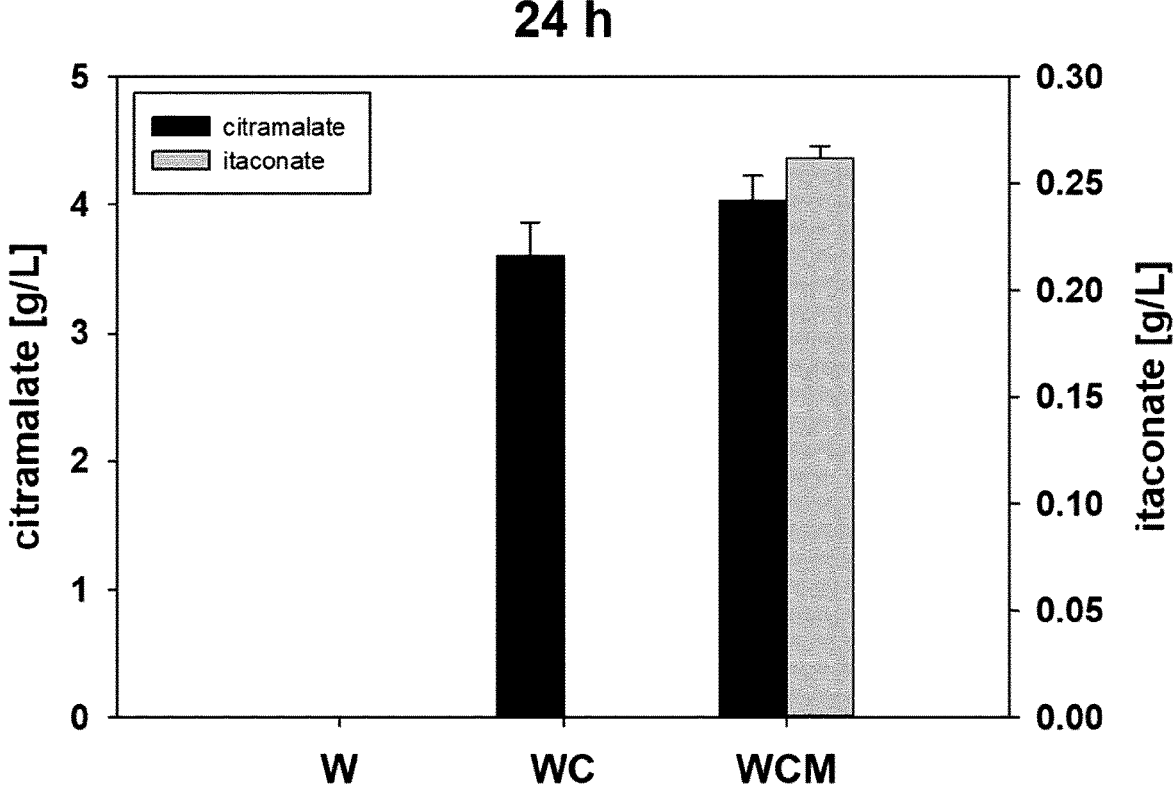
FIG. 2 is a diagram illustrating results of confirming the production of citramalate and itaconate by a recombinant microorganism including a novel itaconic acid production pathway according to the present invention.

As illustrated in FIG. 2, a wild-type *E. coli* W strain as the control group did not produce both citramalate and itaconate. In addition, the WC strain produced citramalate, but did not produce itaconate. On the other hand, it was confirmed that the WCM strain produced both citramalate and itaconate. The results mean that the recombinant microorganism (i.e., WCM strain) into which the novel itaconic acid production pathway is introduced is able to produce itaconate.

Example 3. Construction of Recombinant Microorganisms with Improved Itaconic Acid Productivity Through Deletion of Lactate Production Pathway-Related Gene In order to improve itaconate production efficiency, a recombinant microorganism overexpressing LeuC (SEQ ID NO: 3) and LeuD (SEQ ID NO: 4) was constructed in the WCM strain in which itaconate productivity was confirmed in Example 1, which was referred to as WT. The LeuCD was overexpressed by introducing a recombinant plasmid including a Tac promoter and a synthetic 5' UTR.

In addition, a recombination microorganism in which a lactate production pathway-related gene btuE (SEQ ID NO: 5), leuB (SEQ ID NO: 6), ldhA (SEQ ID NO: 7), adhE (SEQ ID NO: 8), or ackA (SEQ ID NO: 9) was deleted from the WT strain was constructed. The gene deletion was performed by introducing a recombinant vector or DNA fragment containing a FRT-KanR-FRT fragment. The lactate production pathway was competitive with the itaconic acid production pathway, thereby inhibiting the production of itaconate.

Based on the strain overexpressing LeuCD from the WCM strain confirmed to produce itaconate in Example 1, seven recombinant strains from which the constructed lactate production pathway-related gene was deleted were constructed as follows.

WT: *E. coli* W in which CimA3.7 and Mii genes were introduced and LeuCD was overexpressed
B: *E. coli* W in which CimA3.7 and Mii genes were introduced, LeuCD was overexpressed, and btuE was deleted
BL: *E. coli* W in which CimA3.7 and Mii genes were introduced, LeuCD was overexpressed, and btuE and LeuB were deleted
BLL: *E. coli* W in which CimA3.7 and Mii genes were introduced, LeuCD was overexpressed, and btuE, LeuB, and ldhA were deleted BLA: *E. coli* W in which CimA3.7 and Mii genes were introduced, LeuCD was overexpressed, and btuE, LeuB, and adhE were deleted BLLA: *E. coli* W in which CimA3.7 and Mii genes were introduced, LeuCD was overexpressed, and btuE, LeuB, ldhA and adhE were deleted BLLAA: *E. coli* W in which CimA3.7 and Mii genes were introduced, LeuCD was overexpressed, and btuE, LeuB, ldhA, adhE and ackA were deleted The seven recombinant strains constructed were cultured to produce and quantify itaconate. The production and quantification of itaconate were performed in the same manner as in Example 2. However, the M9 medium used in Example 3 was added with 5 g/L of glucose and 5 g/L of a yeast extract. The productivity and yield of citramalate and itaconate of the constructed recombinant strains were illustrated in FIGS. 3A and 3B, respectively.

Figure 3:
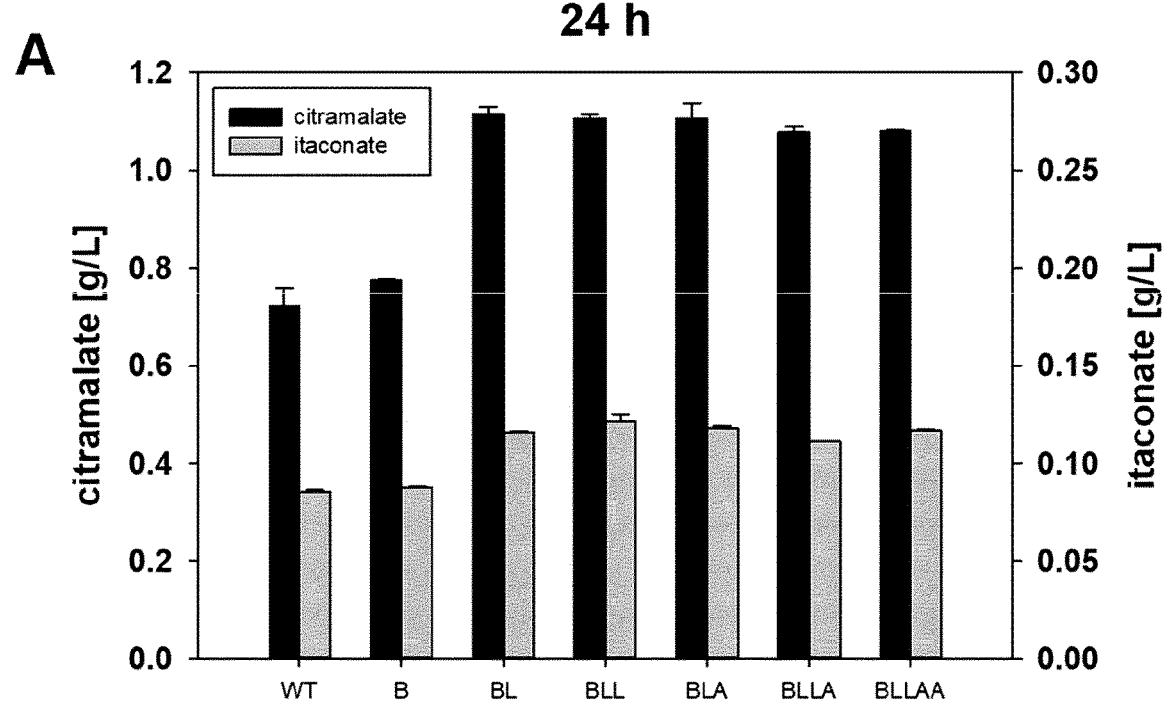
FIG. 3A is a diagram illustrating the production of citramalate and itaconate of a recombinant microorganism including a novel itaconic acid production pathway according to the present invention and with a deleted lactate metabolic pathway-related gene.
FIG. 3B is a diagram illustrating the production yield of citramalate and itaconate of a recombinant microorganism including a novel itaconic acid production pathway according to the present invention and with a deleted lactate metabolic pathway-related gene.
Figure 3:
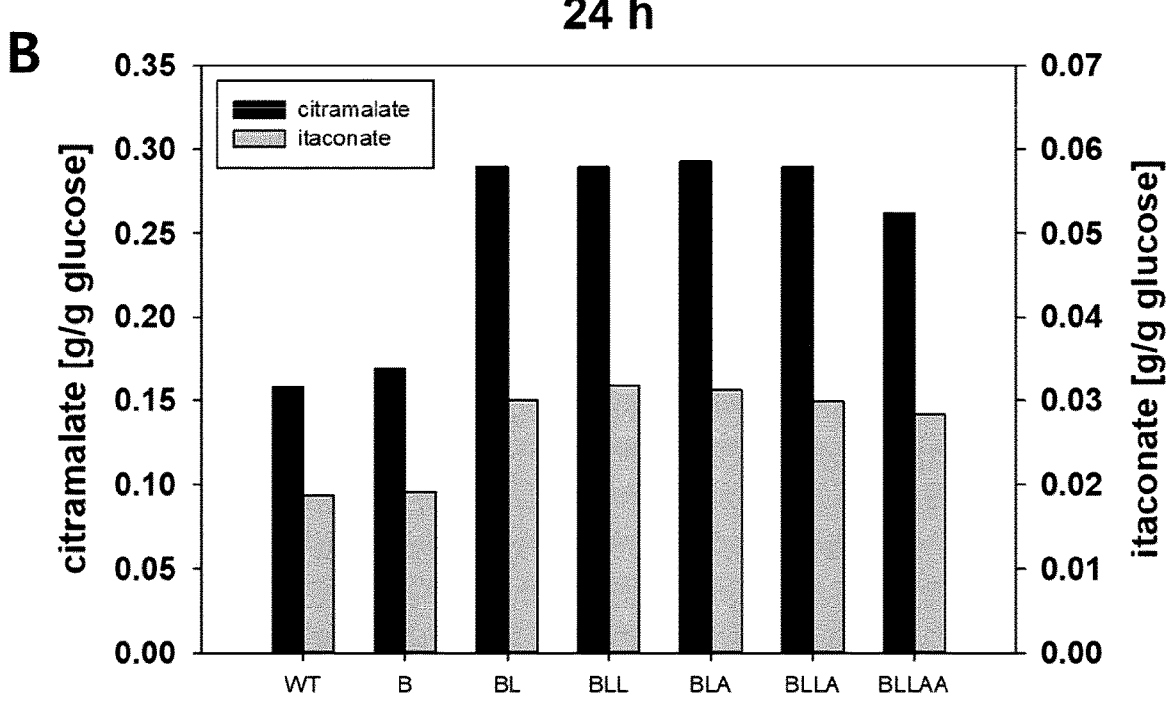

As illustrated in FIGS. 3A and 3B, it was confirmed that the production of citramalate was significantly increased through the overexpression of LeuCD and the deletion of the lactate production pathway of the recombinant strain constructed in Example 3, and accordingly, the production of itaconate was also significantly increased.

Example 4. Construction of Recombinant Microorganisms with Improved Itaconic Acid Productivity Through Deletion of TCA Cycle Introduction Pathway-Related Gene A gltA gene (SEQ ID NO: 10) was deleted from the recombinant strain BLLAA constructed in Example 3 to delete the TCA cycle introduction pathway, which was referred to as a recombinant strain BLLAAG. The deletion of the gltA gene was performed by introducing a recombinant vector or DNA fragment containing the FRT-KanR-FRT fragment in the same manner as the method of deleting the gene in Example 3.

Itaconate was produced and quantified by culturing the constructed recombinant strain BLLAAG and the recombinant strains WT and BLLAA constructed in Example 3. The production and quantification of itaconate were performed in the same manner as in Example 3. The productivity and yield of citramalate and itaconate of the constructed recombinant strains were illustrated in FIGS. 4A and 4B, respectively.

Figure 4:
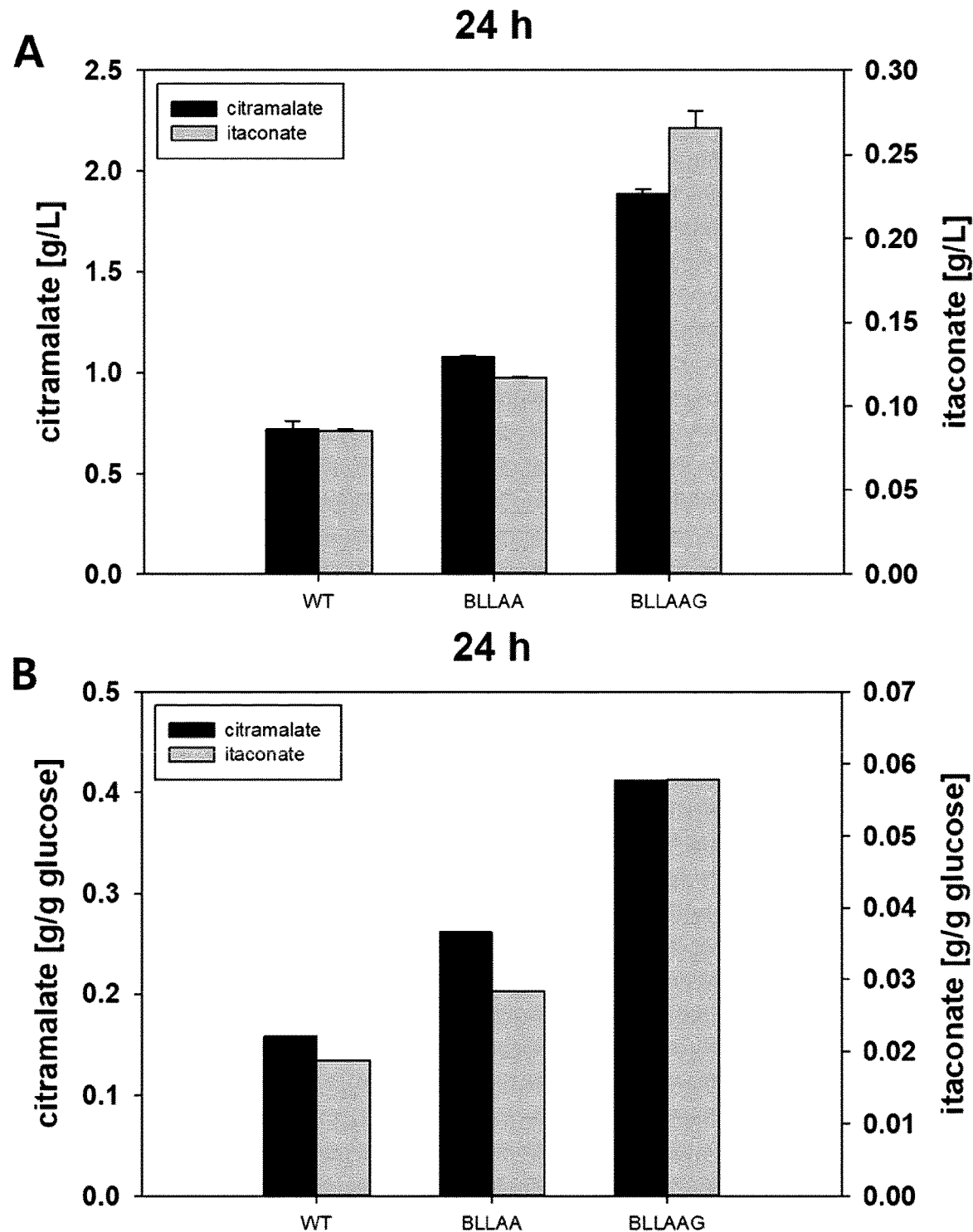
FIG. 4A is a diagram illustrating the production of citramalate and itaconate of a recombinant microorganism including a novel itaconic acid production pathway according to the present invention and with deleted lactate metabolic pathway-related gene and TCA cycle introduction pathway-related gene.
FIG. 4B is a diagram illustrating the production yield of citramalate and itaconate of a recombinant microorganism including a novel itaconic acid production pathway according to the present invention and with deleted lactate metabolic pathway-related gene and TCA cycle introduction pathway-related gene.

As illustrated in FIGS. 4A and 4B, the citramalate yield of the recombinant strain BLLAA increased about 1.66 times higher than that of the recombinant strain WT. In particular, the citramalate yield of the recombinant strain BLLAAG increased about 1.57 times higher than that of the recombinant strain BLLAA and increased about 2.61 times higher than that of the recombinant strain WT. In addition, the itaconate production yield of the recombinant strain BLLAAG increased about 3.05 times higher than that of the recombinant strain WT. It was confirmed that the combined yield of citramalate and itaconate of the recombinant strain BLLAAG was 0.48 g/g glucose, so that itaconate may be produced in high yield.

Overall, the present inventors constructed a novel itaconic acid production pathway and confirmed that the itaconate production yield of the recombinant microorganism into which the novel itaconic acid production pathway was introduced was increased. Furthermore, the itaconate production yield was maximized through additional genetic manipulation of the recombinant microorganism. Therefore, the recombinant microorganism of the present invention may be variously used in the field of itaconate production.

As described above, specific parts of the present invention have been described in detail, and it will be apparent to those skilled in the art that these specific techniques are merely preferred embodiments, and the scope of the present invention is not limited thereto. Therefore, the substantial scope of the present invention will be defined by the appended claims and their equivalents.

---

The invention claimed is:

1. A recombinant vector for producing itaconic acid, comprising an expression cassette comprising a CimA3.7 gene consisting of the nucleotide sequence of SEQ ID NO: 1, and an Mii gene consisting of the nucleotide sequence of SEQ ID NO: 2.

2. The recombinant vector of claim 1, wherein the expression cassette further comprises a 5' UTR consisting of the nucleotide sequence of SEQ ID NO: 12 or 13.

3. The recombinant vector of claim 1, further comprising: wherein the expression cassette further comprises a Tac promoter consisting of the nucleotide sequence of SEQ ID NO: 11.

4. A recombinant Escherichia coli (E. coli) for producing itaconic acid into which the recombinant vector according to claim 1 is introduced.

5. The recombinant E. coli for producing itaconic acid of claim 4, wherein a LeuC gene and a LeuD gene are overexpressed compared to basal expression.

6. The recombinant E. coli for producing itaconic acid of claim 5, wherein a recombinant vector comprising an expression cassette for LeuCD overexpression, compared to basal expression, including a Tac promoter and a 5' UTR is introduced into the recombinant E. coli.

7. The recombinant E. coli for producing itaconic acid of claim 6, wherein the expression cassette for LeuCD over-expression, compared to basal expression, comprises a Tac promoter consisting of the nucleotide sequence of SEQ ID NO: 11 and a 5' UTR consisting of the nucleotide sequence of SEQ ID NO: 14.

8. The recombinant *E. coli* for producing itaconic acid of claim 5, wherein a btuE gene consisting of the nucleotide sequence of SEQ ID NO: 5 is deleted.

9. The recombinant *E. coli* for producing itaconic acid of claim 8, wherein a LeuB gene consisting of the nucleotide sequence of SEQ ID NO: 6 is deleted.

10. The recombinant *E. coli* for producing itaconic acid of claim 9, wherein at least one gene selected from the group consisting of an IdhA gene consisting of the nucleotide sequence of SEQ ID NO: 7; and an adhE gene consisting of the nucleotide sequence of SEQ ID NO: 8 is deleted.

11. The recombinant *E. coli* for producing itaconic acid of claim 10, wherein both the IdhA gene consisting of the nucleotide sequence of SEQ ID NO: 7; and the adhE gene consisting of the nucleotide sequence of SEO ID NO: 8 are deleted, and an ackA gene consisting of the nucleotide sequence of SEO ID NO: 9 is further deleted.

12. The recombinant *E. coli* for producing itaconic acid of claim 11, wherein a gltA gene consisting of the nucleotide sequence of SEO ID NO: 10 is deleted.

13. A method for producing itaconic acid comprising culturing the recombinant *E. coli* for producing itaconic acid according to claim 4.

\* \* \* \* \*

SEQUENCE LISTING

<160> NUMBER OF SEQ ID NOS: 14

<210> SEQ ID NO 1
<211> LENGTH: 1119
<212> TYPE: DNA
<213> ORGANISM: Artificial
<220> FEATURE:
<223> OTHER INFORMATION: CimA3.7

<400> SEQUENCE: 1

```
atgatggttc gcatttttga caccactctg cgcgatgggg aacagactcc cggtgttagt      60
ttaacaccta atgacaagtt agaaatcgca aagaagcttg acgaacttgg tgtagatgtt     120
atcgaggcgg gttcagcagt aacgtcaaaa ggcgagcgcg agggaatcaa attgatcact     180
aaggagggcc tgaacgctga gatttgcagt tttgtacgcg cgcttcccgt cgatattgat     240
gcagctttgg aatgtgatgt tgattcggtt catttggttg tcccaacatc gccgattcac     300
atgaagtata agctgcgcaa gaccgaggac gaagtttag tcacagctct gaaggccgtg     360
gaatatgcta aggaacaggg attaatcgtg gagttatccg cagaggacgc aacacgctca     420
gatgttaact tcttaatcaa acttttcaat gagggtgaga aagtaggagc ggatcgtgta     480
tgtgtttgcg acaccgtcgg agtcttgacc ccgcagaaga gccaagagtt atttaaaaaa     540
attacagaga atgttaactt gcccgtttca gtacattgcc ataatgactt tggtatggca     600
```

-continued

```
acggctaacg cttgttcagc agtactgggt ggcgcagtac agtgtcacgt cacggttaat        660
ggcatcggcg aacgcgctgg caacgcctcc cttgaggagg tcgtagccgc atccaaaatt        720
ttgtacggat atgataccaa gatcaagatg gaaaagcttt atgaggtatc tcgtatcgta        780
tcgcgcttaa tgaaactgcc cgtgcctcct aacaaggcta ttgttggtga taatgcgttt        840
gcccatgagg cagggattca tgttgatggc ttgatcaaaa atactgaaac gtatgagccc        900
attaaacctg aaatggttgg gaatcgccgc cgtatcatct taggtaaaca ttccggtcgc        960
aaagcactga aatacaagtt ggatttgatg gggatcaacg tgtccgacga gcaactgaac       1020
aagatctatg agcgtgtcaa ggagtttgga gatttaggca agtacatctc ggatgccgac       1080
cttttggcta tcgttcgtga ggtaactgga aagttgtaa                              1119
```

<210> SEQ ID NO 2
<211> LENGTH: 1143
<212> TYPE: DNA
<213> ORGANISM: Artificial
<220> FEATURE:
<223> OTHER INFORMATION: Mii

<400> SEQUENCE: 2

```
atgtcagacc agatgcgtat cccctgcgtt atcatgcgcg ccggtacttc taagggaatc         60
tttttgaaag ggaacgacct gccggctgat caagagctgc gcgacaaagt tatccttcgc        120
atttttgggt cccccgatgt tcgccagatc gatggattag cgggggcgga ccccccttacg       180 tctaagctgg ctatcattgg accgtctacc catccggacg cagatgtgga ctacaccttt        240
gcgcaggtat ccattacaga tgcggttgtc gattataatg gtaactgtgg caatatttca        300
gcaggcgttg gcccatttgc aatcgacgag tcgtttgtaa aggcggtcga gccgatgaca        360
cgcgtttgta ttcacaatac gaacacgggt aaattgttgt acgcagaagt cgaggttgaa        420
gatggtaaag caaaagtgag tggcgattgt aaaatcgatg gcgttccggg caccaacgca        480
ccagaattaa tggacttctc tgatacagct ggcgcggcta ctggaaaggt gctgccaact        540
ggtaacgtgg tagatgtttt atcaacgagt aagggtgata tcgatgtaag catcgtggac        600
gttgccaacc cttgcatctt tgtccatgca aaagatgtca atatgacggg cactgagacg        660
ccggatgtca ttaacggaaa cgctgatctt ttggcgtatc ttgaagaaat tcgtgccaag        720
tgctgtgtga agattgggat ggccgctaca gagaaagaag catctgagaa gtctccggct        780
ttcccgatga ttgcgttcgt gactaaaccc gaagattatg ttgatttttc gaccgggaac        840
actatctccg gtgatgatgt ggatctggtt agtcgcttga tgttcatgca agtcttgcat        900
aagacgtacg ctggtactgc gacagcatgt actggatctg cggcgcgtat tcccggtaca        960
atcgtcaacc aagttctgcg tgacacgggc gacgaggata ctgttcgcat cggccaccca       1020
gcgggtgtaa tcccagtagt ctctattgtg aaggacggta aggtcgaaaa ggctgcatta       1080
atccgcacgg cacgtcgcat tatggaggga tatgtgtatg tcgagaaggc taagctggtc       1140
taa                                                                     1143
```

<210> SEQ ID NO 3
<211> LENGTH: 1401
<212> TYPE: DNA
<213> ORGANISM: Artificial
<220> FEATURE:
<223> OTHER INFORMATION: LeuC

<400> SEQUENCE: 3

```
atggctaaga cgttatacga aaaattgttc gacgctcacg ttgtgtacga agccgaaaac         60
```

-continued

```
gaaaccccac tgttatatat cgaccgccac ctggtgcatg aagtgacctc accgcaggcg      120
ttcgatggtc tgcgcgccca cggtcgcccg gtacgtcagc cgggcaaaac cttcgctacc      180
atggatcaca acgtctctac ccagaccaaa gacattaatg cctgcggtga aatggcgcgt      240
atccagatgc aggaactgat caaaaactgc aaagaatttg cgtcgaact gtatgacctg       300 aatcacccgt atcaggggat cgtccacgta atggggccgg aacagggcgt caccttgccg      360
gggatgacca ttgtctgcgg cgactcgcat accgccaccc acggcgcgtt tggcgcactg      420 gccttggta tcggcacttc cgaagttgaa cacgtactgg caacgcaaac cctgaaacag       480
ggccgcgcaa aaaccatgaa aattgaagtc cagggcaaag ccgcgccggg cattaccgca      540
aaagatatcg tgctggcaat tatcggtaaa accggtagcg caggcggcac cgggcatgtg      600
gtggagtttt gcggcgaagc aatccgtgat ttaagcatgg aaggtcgtat gaccctgtgc      660
aatatggcaa tcgaaatggg cgcaaaagcc ggtctggttg caccggacga aaccacgttt      720
aactatgtca aaggccgtct gcatgcgccg aaaggcaaag atttcgacga cgccgttgcc      780
tactggaaaa ccctgcaaac cgacgaaggc gcaactttcg ataccgttgt cactctgcaa      840
gcagaagaaa tttcaccgca ggtcacctgg ggcaccaatc ccggccaggt gatttccgtg      900
aacgacaata ttcccgatcc ggcttcgttt gccgatccgg ttgaacgcgc gtcggcagaa      960
aaagcgctgg cctatatggg gctgaaaccg ggtattccgc tgaccgaagt ggctatcgac      1020
aaagtgttta tcggttcctg taccaactcg cgcattgaag atttacgcgc ggcagcggag      1080
atcgccaaag ggcgaaaagt cgcgccaggc gtgcaggcac tggtggttcc cggctctggc      1140
ccggtaaaag cccaggcgga agcggaaggt ctggataaaa tctttattga agccggtttt      1200
gaatggcgct tgcctggctg ctcaatgtgt ctggcgatga acaacgaccg tctgaatccg      1260
ggcgaacgtt gtgcctccac cagcaaccgt aactttgaag ccgccagggg gcgcggcggg      1320
cgcacgcatc tggtcagccc ggcaatggct gccgctgctg ctgtgaccgg acatttcgcc      1380
gacattcgca acattaaata a                                                 1401
```

<210> SEQ ID NO 4
<211> LENGTH: 606
<212> TYPE: DNA
<213> ORGANISM: Artificial
<220> FEATURE:
<223> OTHER INFORMATION: LeuD

<400> SEQUENCE: 4

```
atggcagaga aatttatcaa acacacaggc ctggtggttc cgctggatgc cgccaatgtc        60
gataccgatg caatcatccc gaaacagttt ttgcagaaag tgacccgtac gggttttggc       120
gcgcatctgt ttaacgactg cgtttttctg gatgaaaaag ccaacagcc aaacccggac        180 ttcgtgctga acttcccgca gtatcagggc gcttccattt tgctggcacg agaaaacttc       240
ggctgtggct cttcgcgtga gcacgcgccc tgggcattga ccgactacgg ttttaaagtg       300
gtgattgcgc gagttttgc tgacatcttc tacggcaata gctttaacaa ccagctgctg        360
ccggtgaaat taagcgatgc agaagtggac gaactgtttg cgctggtgaa agctaatccg       420
gggatccatt cgacgtgga tctggaagcg caagaggtga aagcgggaga gaaaacctat       480
cgctttacca tcgatgcctt ccgccgccac tgcatgatga acggtctgga cagtattggg       540
cttaccttgc agcacgacga cgccattgcc gcttatgaag caaaacaacc tgcgtttatg       600
aattaa                                                                   606
```

-continued

<210> SEQ ID NO 5
<211> LENGTH: 552
<212> TYPE: DNA
<213> ORGANISM: Artificial
<220> FEATURE:
<223> OTHER INFORMATION: btuE

<400> SEQUENCE: 5
atgcaagatt ccattctgac gaccgtagtg aaagatatcg acggtgaagt gaccacgctg        60
gagaagttcg ccggtaatgt gctgttgatt gtcaatgtcg cctcaaagtg tggcttaacg       120
ccgcaatatg agcagttgga gaatattcag aaagcctggg tcgatcgagg tttttatggtg      180 ctgggattcc cgtgcaacca gtttctggaa caagaaccgg gcagcgatga agagattaaa       240
acttactgta ccaccacatg gggggtgacg ttcccgatgt tcagtaagat tgaagttaat       300
ggcgaaggac gccatccgct gtatcaaaaa ttgattgccg cagcgccgac cgcagtcgcg       360
ccggaagaga gcggattcta tgcccgtatg gtcagcaaag gccgtgcacc gctgtacccg       420
gatgatattt tatggaattt tgaaaaattc ctggttggca gggacggaaa agtcatccag       480
cgtttttccc cggatatgac gccggaagat cccattgtga tggaaagcat taaactggcg       540
ttggcaaaat aa                                                           552

<210> SEQ ID NO 6
<211> LENGTH: 1092
<212> TYPE: DNA
<213> ORGANISM: Artificial
<220> FEATURE:
<223> OTHER INFORMATION: LeuB

<400> SEQUENCE: 6
atgtcgaaga attaccatat tgccgtattg ccgggggacg gtattggtcc ggaagtgatg        60
acccaggcgc tgaaagtgct ggatgccgtg cgcaaccgct ttgcgatgcg catcaccacc       120
agccattacg atgtaggcgg cgcagccatt gataaccacg gcaaccact gccgcctgcg        180 acggttgaag gttgtgagca agccgatgcc gtgctgtttg gctcggtagg cggcccgaag       240
tgggaacatt taccaccaga ccagcaacca gaacgcggcg cgctgctgcc tctgcgtaag       300
cacttcaaat tattcagcaa cctgcgcccg gcaaaactgt atcaggggct ggaagcattc       360
tgtccgctgc gtgcagacat tgccgcaaac ggcttcgaca tcctgtgtgt gcgcgaactg       420
accggcggca tctatttcgg tcagccaaaa ggccgcgaag gtagcggaca atatgaaaaa       480
gcctttgata ccgaggtgta tcaccgtttt gagatcgaac gtatcgcccg catcgcgttt       540
gaatctgctc gcaagcgtcg ccacaaagtg acgtcgatcg ataaagccaa cgtgctgcaa       600
tcctctattt tatggcggga gatcgttaac gagatcgcca cggaatacc ggatgtcgaa        660 ctggcgcata tgtacatcga caacgccacc atgcagctga ttaaagatcc atcacagttt       720
gacgttctgc tgtgctccaa cctgtttggc gacattctgt ctgacgagtg cgcaatgatc       780
actggctcga tggggatgtt gccttccgcc agcctgaacg agcaaggttt tggactgtat       840
gaaccggcgg cgggctcggc accagatatc gcaggcaaaa acatcgccaa cccgattgca       900
caaatccttt cgctggcact gctgctgcgt tacagcctgg atgccgatga tgcggcttgc       960
gccattgaac gcgccattaa ccgcgcatta gaagaaggca ttcgcaccgg ggatttagcc      1020
cgtggcgctg ccgccgttag taccgatgaa atgggcgata tcattgcccg ctatgtagca      1080
gaaggggtgt aa                                                          1092

-continued

```
<210> SEQ ID NO 7
<211> LENGTH: 990
<212> TYPE: DNA
<213> ORGANISM: Artificial
<220> FEATURE:
<223> OTHER INFORMATION: ldhA

<400> SEQUENCE: 7
atgaaactcg ccgtttatag cacaaaacag tacgacaaga agtacctgca acaggtgaac      60
gagtcctttg gctttgagct ggaatttttt gactttctgc tgacggaaaa aaccgctaaa     120
actgccaatg gctgcgaagc ggtatgtatt ttcgtaaacg atgacggcag ccgcccggtg     180
ctggaagagc tgaaaaagca cggcgttaaa tatatcgccc tgcgctgtgc cggtttcaat     240
aacgtcgacc ttgacgcggc aaaagaactg gggctgaaag tagtccgtgt tccagcctat     300
gatccagagg ccgttgctga acacgccatc ggtatgatga tgacgctgaa ccgccgtatt     360
caccgcgcgt atcagcgtac ccgtgatgct aacttctctc tggaaggtct gaccggcttt     420
actatgtatg gcaaaacggc aggcgttatc ggtaccggta aaatcggtgt ggcgatgctg     480
cgcattctga aaggttttgg tatgcgtctg ctggcgttcg atccgtatcc aagtgcagcg     540
gcgctggaac tcggtgtgga gtatgtcgat ctgccaaccc tgttctctga atcagacgtt     600
atctctctgc actgcccgct gacaccggaa aactatcatc tgttgaacga agccgccttc     660
gaacagatga aaaatggcgt gatgatcgtc aataccagtc gcggtgcatt gattgattct     720
caggcagcaa ttgaagcgct gaaaaatcag aaaattggtt cgttgggtat ggacgtgtat     780
gagaacgaac gcgatctatt ctttgaagat aaatccaacg acgtgatcca ggatgacgta     840
ttccgtcgcc tgtctgcctg ccacaacgtg ctgtttaccg ggcaccaggc attcctgaca     900
gcagaagctc tgaccagtat ttctcagact acgctgcaaa acttaagcaa tctggaaaaa     960
ggcgaaacct gcccgaacga actggtttaa                                       990

<210> SEQ ID NO 8
<211> LENGTH: 2676
<212> TYPE: DNA
<213> ORGANISM: Artificial
<220> FEATURE:
<223> OTHER INFORMATION: adhE

<400> SEQUENCE: 8
atggctgtta ctaatgtcgc tgaacttaac gcactcgtag agcgtgtaaa aaaagcccag      60
cgtgaatatg ccagtttcac tcaagagcaa gtagacaaaa tcttccgcgc cgccgctctg     120
gctgctgcag atgctcgaat cccactcgcg aaaatggccg ttgccgaatc cggcatgggt     180
atcgtcgaag ataaagtgat caaaaaccac tttgcttctg aatatatcta caacgcctat     240
aaagatgaaa aaacctgtgg tgttctgtct gaagacgaca cttttggtac catcactatc     300
gctgaaccaa tcggtattat ttgcggtatc gttccgacca ctaacccgac ttcaactgct     360
atcttcaaat cgctgatcag tctgaagacc cgtaacgcca ttatcttctc cccgcacccg     420
cgtgcaaaag atgccaccaa caaagcggct gatatcgttc tgcaggctgc tatcgctgcc     480
ggtgctccga agatctgat cggctggatc gatcaacctt ctgttgaact gtctaacgca     540
ctgatgcacc acccagacat caacctgatc ctcgcgactg gtggtccggg catggttaaa     600
gccgcataca gctccggtaa accagctatc ggtgtaggcg cgggcaacac tccagttgtt     660
atcgatgaaa ctgctgatat caaacgtgca gttgcatctg tactgatgtc caaaaccttc     720
gacaacggcg taatctgtgc ttctgaacag tctgttgttg ttgttgactc tgtttatgac     780
```

-continued

```
gctgtacgtg aacgttttgc aacccacggc ggctatctgt tgcagggtaa agagctgaaa       840
gctgttcagg atgttatcct gaaaaacggt gcgctgaacg cggctatcgt tggtcagcca       900
gcctataaaa ttgctgaact ggcaggcttc tctgtaccag aaaacaccaa gattctgatc       960
ggtgaagtga ccgttgttga tgaaagcgaa ccgttcgcac atgaaaaact gtccccgact      1020
ctggcaatgt accgcgctaa agatttcgaa gacgcggtag aaaaagcaga gaaactggtt      1080
gctatgggcg gtatcggtca tacctcttgc ctgtacactg accaggataa ccaaccggct      1140
cgcgtttctt acttcggtca gaaaatgaaa acggcgcgta tcctgattaa caccccagcg      1200
tctcagggtg gtatcggtga cctgtataac ttcaaactcg caccttccct gactctgggt      1260
tgtggttctt ggggtggtaa ctccatctct gaaaacgttg gtccgaaaca cctgatcaac      1320
aagaaaaccg ttgctaagcg agctgaaaac atgttgtggc acaaacttcc gaaatctatc      1380
tacttccgcc gtggctccct gccaatcgcg ctggatgaag tgattactga tggccacaaa      1440
cgtgcgctca tcgtgactga ccgcttcctg ttcaacaatg gttatgctga tcagatcact      1500
tccgtactga aagcagcagg cgttgaaact gaagtcttct tcgaagtaga agcggacccg      1560
accctgagca tcgttcgtaa aggtgcagaa ctggcaaact ccttcaaacc agacgtgatt      1620
atcgcgctgg tggtggttc cccgatggac gccgcgaaga tcatgtgggt tatgtacgaa      1680
catccggaaa ctcacttcga gagctggcg ctgcgcttta tggatatccg taaacgtatc      1740
tacaagttcc cgaaaatggg cgtgaaagcg aaaatgatcg ctgtcaccac cacttctggt      1800
acaggttctg aagtcactcc gtttgcggtt gtaactgacg acgctactgg tcagaaatat      1860
ccgctggcag actatgcgct gactccggat atggcgattg tcgacgccaa cctggttatg      1920
gacatgccga gtccctgtg tgctttcggt ggtctggacg cagtaactca cgccatggaa      1980
gcttatgttt ctgtactggc atctgagttc tctgatggtc aggctctgca ggcactgaaa      2040
ctgctgaaag aatatctgcc agcgtcctac cacgaagggt ctaaaaatcc ggtagcgcgt      2100
gaacgtgttc acagtgcagc gactatcgcg ggtatcgcgt ttgcgaacgc cttcctgggt      2160
gtatgtcact caatggcgca caaactgggt tcccagttcc atattccgca cggtctggca      2220
aacgccctgc tgatttgtaa cgttattcgc tacaatgcga acgacaaccc gaccaagcag      2280
actgcattca gccagtatga ccgtccgcag gctcgccgtc gttatgctga aattgccgac      2340
cacttgggtc tgagcgcacc gggcgaccgt actgctgcta agatcgagaa actgctggca      2400
tggctggaaa cgctgaaagc tgaactgggt attccgaaat ctatccgtga agctggcgtt      2460
caggaagcag acttcctggc gaacgtggat aaactgtctg aagatgcatt cgatgaccag      2520
tgcaccggcg ctaacccgcg ttacccgctg atctccgagc tgaaacagat tctgctggat      2580
acctactacg tcgtgatta tgtagaaggt gaaactgcag cgaagaaaga agctgctccg      2640
gctaaagctg agaaaaaagc gaaaaaatcc gcttaa                              2676
```

```
<210> SEQ ID NO 9
<211> LENGTH: 1203
<212> TYPE: DNA
<213> ORGANISM: Artificial
<220> FEATURE:
<223> OTHER INFORMATION: ackA

<400> SEQUENCE: 9
```

```
atgtcgagta agttagtact ggttctgaac tgcggtagtt cttcactgaa atttgccatc       60
atcgatgcag taaatggtga agagtacctt tctggtttag ccgaatgttt ccacctgccc      120
gaagcacgta tcaaatggaa aatggacggc aataaacagg aagcggcttt aggtgcaggc      180
```

-continued

```
gccgctcaca gcgaagcgct caactttatc gttaatacta ttctggcaca aaaaccagaa      240
ctgtctgcgc agctgactgc tatcggtcac cgtatcgtac acggcggcga aaagtatacc      300
agctccgtag tgatcgatga gtctgttatt cagggtatca aagatgcagc ttcttttgca      360
ccgctgcaca acccggctca cctgatcggt atcgaagaag ctctgaaatc tttcccacag      420
ctgaaagaca aaaacgttgc tgtatttgac accgcgttcc accagactat gccggaagag      480
tcttacctct acgccctgcc ttacaacctg tacaaagagc acggcatccg tcgttacggc      540
gcgcacggca ccagccactt ctatgtaacc caggaagcgg caaaaatgct gaacaaaccg      600
gtagaagaac tgaacatcat cacctgccac ctgggcaacg gtggttccgt ttctgctatc      660
cgcaacggta aatgcgttga cacctctatg ggcctgaccc cgctggaagg tctggtcatg      720
ggtacccgtt ctggtgatat cgatccggcg atcatcttcc acctgcacga caccctgggc      780
atgagcgttg acgcaatcaa caaactgctg accaaagagt ctggcctgct gggtctgacc      840
gaagtgacca gcgactgccg ctatgttgaa gacaactacg cgacgaaaga agacgcgaag      900
cgcgcaatgg acgtttactg ccaccgcctg gcgaaataca tcggtgccta cactgcgctg      960
atggatggtc gtctggacgc tgttgtattc actggtggta tcggtgaaaa tgccgcaatg     1020
gttcgtgaac tgtctctggg caaactgggc gtgctgggct ttgaagttga tcatgaacgc     1080
aacctggctg cacgtttcgg caaatctggt ttcatcaaca aagaaggtac ccgtcctgcg     1140
gtggttatcc caaccaacga agaactggtt atcgcgcaag acgcgagccg cctgactgcc     1200
tga                                                                   1203

<210> SEQ ID NO 10
<211> LENGTH: 1284
<212> TYPE: DNA
<213> ORGANISM: Artificial
<220> FEATURE:
<223> OTHER INFORMATION: gltA

<400> SEQUENCE: 10
atggctgata caaaagcaaa actcaccctc aacgggggata cagctgttga actggatgtg       60
ctgaaaggca cgctgggtca agatgttatt gatatccgta ctctcggttc aaaaggtgtg      120
ttcacctttg acccaggctt cacttcaacc gcatcctgcg aatctaaaat tactttatt      180 gatggtgatg aaggtatttt gctgcaccgc ggtttcccga tcgatcagct ggcgaccgat      240
tctaactacc tggaagtttg ttacatcctg ctgaatggtg aaaaaccgac tcaggaacag      300
tatgacgaat ttaaaactac ggtgacccgt cataccatga tccacgagca gattacccgt      360
ctgttccatg ctttccgtcg cgactcgcat ccaatggcag tcatgtgtgg tattaccggc      420
gcgctggcgg cgttctatca cgactcgctg atgttaaca atcctcgtca ccgtgaaatt      480
gccgcgttcc gcctgctgtc gaaaatgccg accatggccg cgatgtgtta caagtattcc      540
attggtcagc catttgttta cccgcgcaac gatctctcct acgccggtaa cttcctgaat      600
atgatgttct ccacgccgtg cgaaccgtat gaagttaatc cgattctgga acgtgctatg      660
gaccgtattc tgatcctgca cgctgaccat gaacagaacg cctctacctc caccgtgcgt      720
accgctggct cttcgggtgc gaacccgttt gcctgtatcg cagcaggtat tgcttcactg      780
tggggacctg cgcacggcgg tgctaacgaa gcggcgctga aaatgctgga agaaatcagc      840
tccgttaaac acattccgga atttgttcgt cgtgcgaaag acaaaaatga ttctttccgc      900
ctgatgggct tcggtcaccg cgtgtacaaa aattacgacc cgcgcgccac cgtaatgcgt      960
```

-continued

```
gaaacctgcc atgaagtgct gaaagagctg ggcacgaagg atgacctgct ggaagtggct    1020
atggagctgg aaaacatcgc gctgaacgac ccgtacttta tcgagaagaa actgtacccg    1080
aacgtcgatt tctactctgg tatcatcctg aaagcgatgg gtattccgtc ttccatgttc    1140
accgtcattt tcgcaatggc acgtaccgtt ggctggatcg cccactggag cgaaatgcac    1200
agtgacggta tgaagattgc ccgtccgcgt cagctgtata caggatatga aaaacgcgac    1260
tttaaaagcg atatcaagcg ttaa                                            1284

<210> SEQ ID NO 11
<211> LENGTH: 55
<212> TYPE: DNA
<213> ORGANISM: Artificial
<220> FEATURE:
<223> OTHER INFORMATION: tac promotor

<400> SEQUENCE: 11
ttgacaatta atcatcggct cgtataatgt gtggaattgt gagcggataa caatt          55

<210> SEQ ID NO 12
<211> LENGTH: 25
<212> TYPE: DNA
<213> ORGANISM: Artificial
<220> FEATURE:
<223> OTHER INFORMATION: cimA3.7 5'UTR

<400> SEQUENCE: 12
aaacaaaaaa aaaggagcat cctca                                           25

<210> SEQ ID NO 13
<211> LENGTH: 25
<212> TYPE: DNA
<213> ORGANISM: Artificial
<220> FEATURE:
<223> OTHER INFORMATION: mii 5'UTR

<400> SEQUENCE: 13
aaacacaaga aaaggagcat ccaga                                           25

<210> SEQ ID NO 14
<211> LENGTH: 25
<212> TYPE: DNA
<213> ORGANISM: Artificial
<220> FEATURE:
<223> OTHER INFORMATION: leuCD 5'UTR

<400> SEQUENCE: 14
aaagaatcgg aaaggagcat caaca                                           25
```